United States Patent [19]
Critchley et al.

[11] Patent Number: 5,206,020
[45] Date of Patent: Apr. 27, 1993

[54] SYNTHETIC PSEUDOCERAMIDE AND COSMETIC COMPOSITIONS THEREOF

[75] Inventors: Peter Critchley, Bedford; Anthony V. Rawlings, Raunds, Northants, both of England; Ian R. Scott, Allendale, N.J.

[73] Assignee: Elizabeth Arden Company, Division of Conopco, Inc., New York, N.Y.

[21] Appl. No.: 820,576

[22] Filed: Jan. 14, 1992

[30] Foreign Application Priority Data

Jan. 15, 1991 [GB] United Kingdom ............... 9100816

[51] Int. Cl.$^5$ .................. A61K 7/00; A61K 7/48; A61K 21/685
[52] U.S. Cl. .................................. 424/401; 424/59; 424/61; 424/69; 424/70; 424/501; 514/24; 514/25; 514/119
[58] Field of Search ............... 424/401, 59, 60, 69, 424/70; 514/24, 25, 119, 136, 670, 671, 676; 536/18.7

[56] References Cited

FOREIGN PATENT DOCUMENTS

| | | |
|---|---|---|
| 0097059 | 12/1983 | European Pat. Off. |
| 0118316 | 9/1984 | European Pat. Off. |
| 0122152 | 10/1984 | European Pat. Off. |
| 0227994 | 7/1987 | European Pat. Off. |
| 0282816 | 9/1988 | European Pat. Off. |
| 0398272 | 11/1990 | European Pat. Off. |
| 63-185441 | 1/1987 | Japan . |
| 63-185442 | 1/1987 | Japan . |
| 63-178842 | 7/1988 | Japan . |
| 63-192703 | 8/1988 | Japan . |
| 420883 | 12/1934 | United Kingdom . |

OTHER PUBLICATIONS

Imokawa et al. J. Soc. Cosmet. Chem. 40,273–285 Sep.-/Oct. 1989.
Meyer et al. J. Med. Chem. 1991, 34, 1377–1383.
European Search Report completed Apr. 22, 1992.
Chemical Abstracts, vol. 111, No. 12, Sep. 18, 1989, K. Tsubone "2-(2-Hydroxy-N-alkyl)acyloxypropylamion) ethylphosphate ester salts for the manufacture of pharmaceutical, cosmetic and agrochemical liposomes" p. 354, Abstract No. 102703j.
J. Invest. Derm., Fulmer & Kramer, (1986), 86, pp. 598–602.
Tupker R. A. et al, Acta Derm. Venereol. Stockh (1990), 70, pp. 1–5.

Primary Examiner—Thurman K. Page
Assistant Examiner—Neil Levy
Attorney, Agent, or Firm—Milton L. Honig

[57] ABSTRACT

Novel pseudoceramides are compounds with a general structure (2):

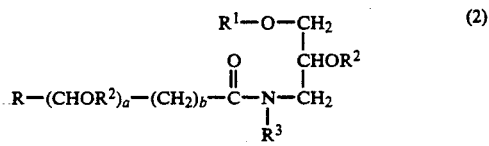

In this formula a is 0 or 1, b is 0 or 1 but if a is 0, b is also 0 and R has 1 to 8 carbon atoms. The substituents R and $R^1$ are a range of substituted or unsubstituted aliphatic hydrocarbon substituents. $R^2$ is hydrogen, a sugar residue, a sulphate residue or a phosphate residue. $R^3$ is hydrogen or a fairly short chain hydrocarbon substituent which in turn may be substituted. All of the substituents R—$R^3$ are more fully defined in claim 1. These novel compounds are effective to improve water barrier function of the stratum corneum. They may be incorporated into compositions for topical application to human skin, hair and nails. A synthetic route for obtaining the novel compounds is described.

6 Claims, No Drawings

SYNTHETIC PSEUDOCERAMIDE AND COSMETIC COMPOSITIONS THEREOF

FIELD OF THE INVENTION

The invention relates to novel pseudoceramides, their synthesis and use in compositions for topical application to human skin, hair or nails.

BACKGROUND TO THE INVENTION AND PRIOR ART

It is generally understood that ceramides present within the intercellular lipid lamellae of the stratum corneum have an important role in the production and maintenance of the water permeability barrier of the skin. Ceramides, or substances closely related to them, have been disclosed as components of skin care compositions. In particular, Kao Corporation in EP 0227994 and EP 0282816 disclose synthetic analogues of ceramides which, to a significant extent, have properties similar to natural ceramides, but are relatively cheaper to produce. However, the degree of skin benefit attributable to such synthetic ceramides or analogues thereof is limited to the extent that they do not fully mimic the natural ceramides of the skin, some of which contain N-acylated hydroxyfatty acids. Thus the general formula of molecules disclosed by Kao in EP 0227994 is structure (1):

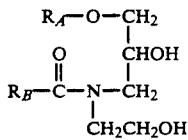

In JP-A-63-192703, Kao Corporation disclose a skin composition which contains extracted naturally occurring skin ceramides including either phytosphingosines or α-hydroxy fatty acid-containing ceramides. Synthetic hydroxylated ceramide structures are not disclosed. A further family of ceramides of the type found in skin, is disclosed in EP 097 059 (Unilever). This highlights the vital role played by ω-(O-linoleoyl) ceramides in the water barrier of the skin.

Fulmer & Kramer, in J. Invest. Derm. (1986) 86, 598–602, have observed that there is a relative deficiency of phytosphingosine-containing ceramide in detergent-induced dry skin conditions. Also, it is well documented that the stratum corneum water barrier function is impaired under such conditions (Tupker R.A. et al., Acta Derm. Venereol. Stockh [1990], 70, 1–5).

We have now discovered that the number of hydroxyl groups present within a ceramide structure is highly relevant to its influence on the water barrier properties. Furthermore, we have shown that synthetic hydroxylated ceramides, hereinafter referred to as "pseudoceramides" can be synthesised at lower cost than extracting the natural homologues from natural sources, and that these pseudoceramides posses properties necessary to improve water barrier function of the stratum corneum.

DEFINITION OF THE INVENTION

Accordingly, the invention provides a pseudo ceramide having the structure (2):

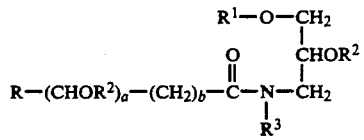

where

R represents a linear or branched, saturated or unsaturated, hydroxylated or non-hydroxylated, phosphorylated or non-phosphorylated, sulphated or non-sulphated aliphatic hydrocarbon group having from 1 to 49 carbon atoms;

$R^1$ represents a linear or branched, saturated or unsaturated, hydroxylated or non-hydroxylated, phosphorylated or non-phosphorylated, sulphated or non-sulphated aliphatic hydrocarbon group having from 1 to 28 carbon atoms;

$R^2$ represents H, a sugar residue, a sulphate residue or a phosphate residue $P_i$;

$P_i$ represents the group:

$R^3$ represents H, or the sub group (3):

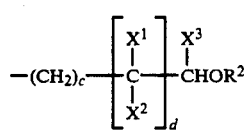

$X^1$, $X^2$ and $X^3$ each individually represent H, $C_{1-5}$ alkyl or $C_{1-5}$ hydroxyalkyl;

a is 0 or 1 b is 0 or 1 c is 0 or an integer of from 1 to 4 d is 0 or 1;

provided that if a is 0, b is also 0 and the group R has from 1 to 8 carbon atoms.

DISCLOSURE OF THE INVENTION

The Pseudoceramide

The invention provides a class of pseudoceramides having the general structure (2) as hereinbefore defined.

With reference to structure (2), the group R preferably represents an aliphatic hydrocarbon group having from 12 to 32 carbon atoms.

Specific examples of pseudoceramides according to the invention are those having the structures (4) to (16), as set out below:

N-(2-hydroxy-3-hexadecyloxypropyl)-N-(2-hydroxyethyl)-2-hydroxyhexadecamide having the structure (4)

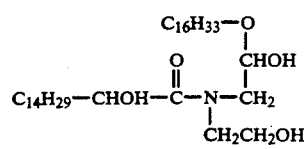

N-(2-hydroxy-3-hexadecyloxypropyl)-N-(2-O-glucopyranosyl)ethyl-2-hydroxyhexadecamide having the structure (5)

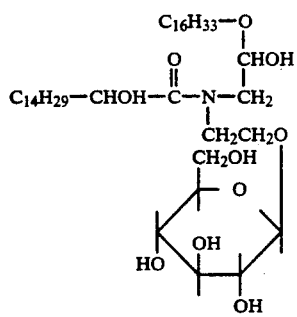

N-(2-hydroxy-3-hexadecyloxypropyl)-N-(2-hydroxyethyl)-3-hydroxy-hexadecamide having the structure (6)

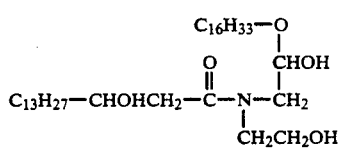

N-(2-hydroxy-3-hexadecyloxypropyl)-N-(2-hydroxyethyl)-2-hydroxy-octamide having the structure (7):

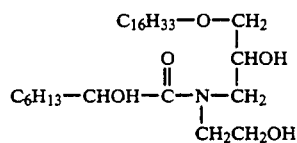

N-(2-hydroxy-3-nonyloxypropyl)-N-(2-sulphoethyl)-2-hydroxydecamide having the structure (8)

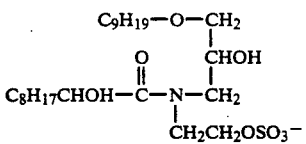

N-(2-hydroxy-3-hexadecyloxypropyl)-N-(2-hydroxyethyl)octamide having the structure (9):

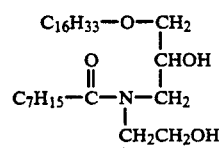

N-(2-hydroxy-3-hexadecyloxypropyl)-N-(2-hydroxyethyl)-3-hydroxyhexadecamide having the structure (10):

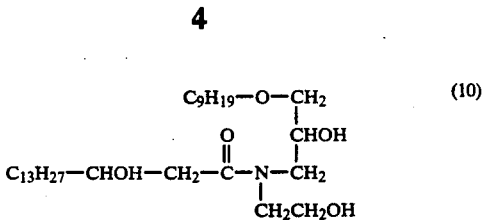

N-(2-hydroxy-3-nonyloxypropyl)-N-(2-sulphoethyl)-2-hydroxy-decamide having the structure (11):

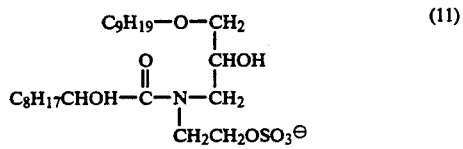

N-(2-hydroxy-3-hexadecyloxypropyl)-N-(2-sulphoethyl)-2-hydroxyhexadecamide having the structure (12):

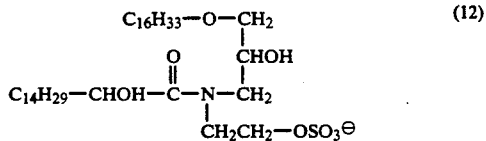

N-(2-hydroxy-3-hexadecyloxypropyl)-N-(2-phosphoethyl)-2-hydroxyhexadecamide having the structure (13):

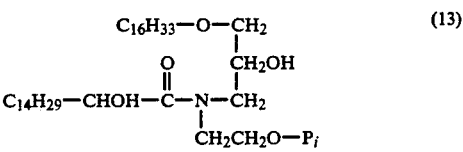

N-(2-hydroxy-3-tritriacontyloxypropyl)-N-(2-phosphoethyl)-2-hydroxypentacosamide having the structure (14):

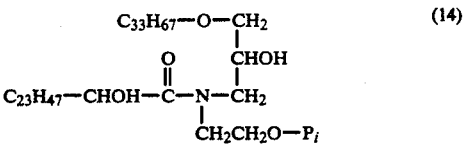

N-(2-hydroxy-3-hexadecyloxypropyl)-N-(2-hydroxyethyl)-3-hydroxyoctamide having the structure (15):

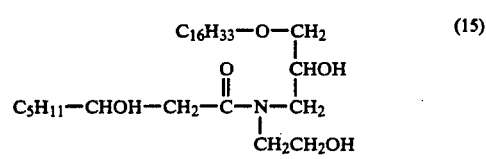

N-(2-hydroxy-3-hexadecyloxypropyl)-N-(3-methyl-4-hydroxybutyl)-2-hydroxyhexadecamide having the structure (16):

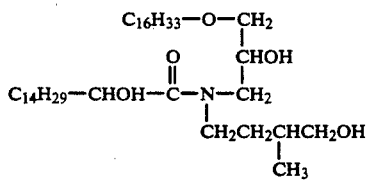

(16)

SYNTHESIS OF THE PSEUDOCERAMIDES

The pseudoceramides according to the invention can conveniently be synthesised by ring opening the terminal epoxide ring of a glycidyl ether, using an amine, to provide a secondary amine. This secondary amine is then acylated with an ester or an acid chloride of a hydroxylated fatty acid or a nonhydroxylated fatty acid with less than 10 carbon atoms, to obtain the required pseudoceramide. Initial formation of a glycidyl ether may be carried out in several ways. One route uses an alcohol, epichlorohydrin and 50% aqueous tetrabutylammonium bromide in hexane with 50% aqueous sodium hydroxide.

SPECIFIC EXAMPLES OF THE SYNTHESIS

Synthesis of N-(2-Hydroxy-3-Hexadecyloxypropyl)-N-(2-Hydroxyethyl)-2-Hydroxyhexadecamide (4)

The pseudoceramide having the structure (4), which is the structure (2) in which $R=C_{14}H_{29}$, $R^1=C_{16}H_{33}$, every $R^2=H$, $R^3=CH_2CH_2OH$, $a=1$ and $b=0$, is prepared in accordance with the following scheme:

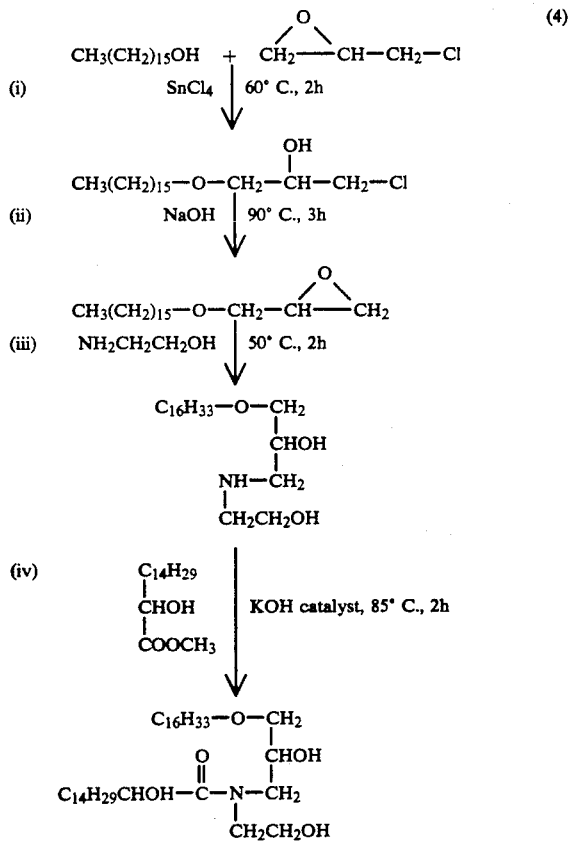

(4)

Further details of the stages of the synthesis are as follows.

Synthesis of 3-Chloro-2-Hydroxypropyl Hexadecyl Ether

Hexadecanol (10.0 g, 0.0412 mole) and stannic chloride (0.04 g, 0.16 mmoles) were heated to 60° C. Epichlorohydrin (3.82 g, 0.0412 moles (was added over 1 hour and the reaction conditions kept constant for another hour. The hot product was extracted with 5% aqueous HCl and ether. The ether was concentrated to a white solid product (yield=75%).

IR (neat, in cm$^{-1}$); 3420(br), 2920(s) 2880(s).

$^1$H NMR (200 MHz, CDCl$_3$ with TMS)δ0.88 (t,j=8 Hz 3H), 1.20 (brs,30H), 1.6 (br m,2H), 3.5 (m,2H) 3.95 (m,2H).

Synthesis of Hexadecyl Glycidyl Ether

To a solution of 3-chloro-2-hydroxypropyl hexadecyl ether (10 g, 0.0311 moles in 20 mls water at 90° C. under argon was added a 50% solution of sodium hydroxide (1.37 g, 0.0343 moles) in 10 mls water over 15 minutes. The reaction was heated under the same conditions for 3 additional hours. Sample was purified by distillation (yield=60%). Upon cooling a white solid formed.

b.p.=175°–180° C. @ 0.8 mmHg

IR (nujol, in cm$^{-1}$) 2920(vs), 2880(vs), 1110(s), 840(m)

$^1$H NMR (200 MHz, CDCl$_3$ with TMS)δ 0.89 (t,J=8 Hz,3H), 1.3 (br s,24H), 1.6 (br m,2H), 2.6 (dd, J=2.3 Hz, J=5.7 Hz,2H), 2.8 (dd, J=4 Hz, J=5.7 Hz,2H), 3.1(m,1H), 3.5(m,4H).

$^{13}$C NMR (50 MHz,CDCl$_3$ with TMS) ppm 71.62, 71.37, 31.86, 29.54, 22.62, 14.03.

m/e (GC/EI/MS) M+298.

Synthesis of N-(2-Hydroxyethyl)-3-Hexadecyloxypropyl Amine

To a solution of hexadecyl glycidyl ether (5.00 g, 0.0168 moles) in 10 mls ethanol at 50° C. under argon was added dropwise ethanol amine (5.12 g, 0.0838 moles) in 10 mls ethanol. The reaction proceeded for 2 hours. The solvent and excess ethanol amine were removed under vacuum. The white solid was recrystallised in acetone (yield=67%).

m.p.=74°–75° C.

IR (nujol, in cm$^{-1}$): 3450(m), 3310(w), 2900(vs), 2850(vs).

$^1$H NMR (200MHz, CDCl$_3$/CD$_3$OD with TMS)δ 0.80 t,J=8 Hz,3H), 1.20 (br s,28H), 1.6 (br m,2H), 2.7 (m,2H), 3.40 (dd,J=5.4 Hz,J=14.5 Hz,4H), 3.7 (br t,J=5.4 Hz,3H), 3.8 (m,2H), 4.50 (s,1H).

$^{13}$C NMR (50 MHz, CDCl$_3$/CD$_3$OD with TMS) ppm 73.07, 71.27, 68.28, 60.00, 51.62, 50.63, 31.46, 29.20, 13.44.

m/e (TSP/MS) MH+360.

Synthesis of Methyl-2-Hydroxyhexadecanoate 2-hydroxyhexadecanoic acid (10.0 g, 0.0367 moles) and 8.40 g acidic resin were refluxed in 250 mls methanol for 20 hours. The solution was decolorized, filtered and concentrated giving a white solid (yield=85%)

$^1$H NMR (200 MHz CDCl$_3$ with TMS)δ 0.88 (t,J=8 Hz,3H) 1.35 (br s,30H), 3.80 (s,3H).

$^{13}$C NMR (50 MHz CDCl$_3$ with TMS) ppm: 175.75, 70.37, 52.22, 34.29, 31.83, 29.47, 24.67, 13.98.

m/e (GC/CI/MS) M+287.

Synthesis of Pseudoceramide of Structure (4)

N-(2-hydroxyethyl)-3-hexadecyloxypropyl amine (1.15 g, 3.2 mmoles) and potassium hydroxide (0.010 g, 0.18 mmoles) were heated to 85° C. @20 Torr. Over 15 minutes were added methyl-2-hydroxyhexadecanoate (0.921 g, 3.22 mmoles). The reaction proceeded under the same conditions over the next 2 hours. Upon cooling an offwhite solid precipitated. The solid was recrystallised in hot hexane to give a white solid (yield=75%). Sample contains four diastereomers and gave complex NMR analysis.

m.p. 55°-57° C.

IR (Nujol, in $cm^{-1}$): 3330(br) 2920(vs), 2870(vs) 1625(s), 1050(m).

m/e(FAB/MS) MH+614.

A possible alternative to the first two steps is the formation of hexadecyl glycidyl ether directly from hexadecanol and epichlorohydrin in the presence of boron trifluoride.

DEFINITION OF COMPOSITIONS OF THE INVENTION

The invention also provides a composition for topical application to human skin which comprises:
i. an effective amount of a pseudoceramide having the structure (2); and
ii. a cosmetically acceptable vehicle for the synthetic ceramide.

DISCLOSURE OF THE COMPOSITION

The composition according to the invention comprises in its simplest form a special pseudoceramide and a vehicle therefor to enable the amide derivative to be dispersed onto the skin and distributed thereon.

The Pseudoceramide

The composition according to the invention comprises an effective amount of a pseudoceramide, or a mixture thereof, having the structure (2) as herein defined. Preferred examples of the pseudoceramide having the structure (2) are those having the structures (5) to (16), as herein defined.

The amount of the pseudoceramide, or a mixture thereof, present in the composition according to the invention is from 0.00001 to 50%, preferably from 0.001 to 20% and most preferably from 0.1 to 10% by weight.

The Cosmetically Acceptable Vehicle

The composition according to the invention also comprises a cosmetically acceptable vehicle to act as a dilutant, dispersant or carrier for the pseudoceramide in the composition, so as to facilitate its distribution when the composition is applied to the skin and/or hair.

Vehicles other than water can include liquid or solid emollients, solvents, humectants, thickeners and powders. Examples of each of these types of vehicle, which can be used singly or as mixtures of one or more vehicles, are as follows:

Emollients, such as stearyl alcohol, glyceryl monoricinoleate, glyceryl monostearate, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, tallow, lard, olive oil, palm kernel oil, rapeseed oil, safflower seed oil, evening primrose oil, soybean oil, sunflower seed oil, avocado oil, olive oil, sesame seed oil, coconut oil, arachis oil, castor oil, acetylated lanolin alcohols, petroleum jelly, mineral oil, butyl myristate, isostearic acid, palmitatic acid, isopropyl linoleate, lauryl lactate, myristyl lactate, decyl oleate, myristyl myristate; Propellants, such as trichlorofluoromethane, dichlorodifluoromethane, dichlorotetrafluoroethane, monochlorodifluoromethane, trichlorotrifluoroethane, propane, butane, isobutane, dimethyl ether, carbon dioxide, nitrous oxide;

Solvents, such as ethyl alcohol, methylene chloride, isopropanol, acetone, ethylene glycol monoethyl ether, diethylene glycol monobutyl ether, diethylene glycol monoethyl ether, dimethyl sulphoxide, dimethyl formamide, tetrahydrofuran;

Powders, such as chalk, talc, fullers earth, kaolin, starch, gums, colloidal silica sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, ethylene glycol monostearate.

The cosmetically acceptable vehicle will usually form from 10 to 99.9%, preferably from 50 to 99% by weight of the emulsion, and can, in the absence of other cosmetic adjuncts, form the balance of the composition.

OPTIONAL SKIN BENEFIT MATERIALS AND COSMETIC ADJUNCTS

A particularly convenient form of the composition according to the invention is an emulsion, in which case an oil or oily material will normally be present, together with an emulsifier to provide either a water-in-oil emulsion or an oil-in-water emulsion, depending largely on the average hydrophilic-lyophilic balance (HLB) of the emulsifier employed.

Oil or Oily Material

The composition according to the invention can optionally comprise one or more oils or other materials having the properties of an oil.

Examples of suitable oils include mineral oil and vegetable oils, and oil materials, such as those already proposed herein as emollients. Other oils or oily materials include silicone oils, both volatile and non-volatile, such as polydimethyl siloxanes.

The oil or oily material, when present for the purposes for forming an emulsion, will normally form up to 90%, preferably from 10 to 80% by volume of the composition.

Emulsifier

The composition according to the invention can also optionally comprise one or more emulsifiers the choice of which will normally determine whether a water-in-oil or and oil-in-water emulsion is formed.

When a water-in-oil emulsion is required, the chosen emulsifier or emulsifiers should normally have an average HLB value of from 1 to 6. When an oil-in water emulsion is required, a chosen emulsifier or emulsifiers should have an average HLB value of >6.

Examples of suitable emulsifiers are set below in Table 1 in which the chemical name of the emulsifiers is given together with an example of a trade name as commercially available, and the average HLB value.

TABLE 1

| Chemical Name of Emulsifier | Trade Name | HLB Value |
|---|---|---|
| Sorbitan trioleate | Arlacel 85 | 1.8 |
| Sorbitan tristearate | Span 65 | 2.1 |
| Glycerol monooleate | Aldo MD | 2.7 |
| Glycerol monostearate | Atmul 84S | 2.8 |
| Glycerol monolaurate | Aldo MC | 3.3 |
| Sorbitan sesquioleate | Arlacel 83 | 3.7 |
| Sorbitan monooleate | Arlacel 80 | 4.3 |
| Sorbitan monostearate | Arlacel 60 | 4.7 |
| Poloxyethylene (2) stearyl ether | Brij 72 | 4.9 |
| Poloxyethylene sorbitol beeswax derivative | G-1702 | 5 |
| PEG 200 dilaurate | Emerest 2622 | 6.3 |
| Sorbitan monopalmitate | Arlacel 40 | 6.7 |
| Polyoxyethylene (3.5) nonyl phenol | Emulgen 903 | 7.8 |
| PEG 200 monostearate | Tegester PEG 200 MS | 8.5 |
| Sorbitan monolaurate | Arlacel 200 | 8.6 |
| PEG 400 dioleate | Tegester PEG 400-DO | 8.8 |
| Polyoxyethylene (5) monostearate | Ethofat 60-16 | 9.0 |
| Polyoxyethylene (4) sorbitan monostearate | Tween 61 | 9.6 |
| Polyoxyethylene (4) lauryl ether | Brij 30 | 9.7 |
| Polyoxyethylene (5) sorbitan monooleate | Tween 81 | 10.0 |
| PEG 300 monooleate | Neutronyx 834 | 10.4 |
| Polyoxyethylene (20) sorbitan tristearate | Tween 65 | 10.5 |
| Polyoxyethylene (20) sorbitan trioleate | Tween 85 | 11.0 |
| Polyoxyethylene (8) monostearate | Myrj 45 | 11.1 |
| PEG 400 monooleate | Emerest 2646 | 11.7 |
| PEG 400 monostearate | Tegester PEG 400 | 11.9 |
| Polyoxyethylene 10 monooleate | Ethofat 0/20 | 12.2 |
| Polyoxyethylene (10) stearyl ether | Brij 76 | 12.4 |
| Polyoxyethylene (10) cetyl ether | Brij 56 | 12.9 |
| Polyoxyethylene (9.3) octyl phenol | Triton X-100 | 13.0 |
| Polyoxyethylene (4) sorbitan monolaurate | Tween 21 | 13.3 |
| PEG 600 monooleate | Emerest 2660 | 13.7 |
| PEG 1000 dilaurate | Kessco | 13.9 |
| Polyoxyethylene sorbitol lanolin derivative | G-1441 | 14.0 |
| Polyoxyethylene (12) lauryl ether | Ethosperse LA-12 | 14.4 |
| PEG 1500 dioleate | Pegosperse 1500 | 14.6 |
| Polyoxyethylene (14) laurate | Arosurf HFL-714 | 14.8 |
| Polyoxyethylene (20) sorbitan monostearate | Tween | 14.9 |
| Polyoxyethylene 20 sorbitan monooleate | Tween 80 | 15.0 |
| Polyoxyethylene (20) stearyl ether | Brij 78 | 15.3 |
| Polyoxyethylene (20) sorbitan monopalmitate | Tween 40 | 15.6 |
| Polyoxyethylene (20) cetyl ether | Brij 58 | 15.7 |
| Polyoxyethylene (25) oxypropylene monostearate | G-2162 | 16.0 |
| Polyoxyethylene (20) sorbitol monolaurate | Tween 20 | 16.7 |
| Polyoxyethylene (23) lauryl ether | Brij 35 | 16.9 |
| Polyoxyethylene (50) monostearate | Myrj 53 | 17.9 |
| PEG 4000 monostearate | Pegosperse 4000 | 18.7 |

TABLE 1-continued

| Chemical Name of Emulsifier | Trade Name | HLB Value |
|---|---|---|
| | MS | |

The foregoing list of emulsifiers is not intended to be limiting and merely exemplifies selected emulsifiers which are suitable for use in accordance with the invention.

It is to be understood that two or more emulsifiers can be employed if desired.

The amount of emulsifier or mixtures thereof, to be incorporated in the composition of the invention, when appropriate is from 1 to 50%, preferably from 2 to 20% and most preferably from 2 to 10% by weight of the composition.

Water

The composition of the invention can also comprise water, usually up to 98%, preferably from 5 to 80% by volume.

Silicone Surfactant

The composition of the invention can also optionally comprise a high molecular weight silicone surfactant which can also act as an emulsifier, in place of or in addition to the optional emulsifier(s) already mentioned.

The silicone surfactant is a high molecular weight polymer of dimethyl polysiloxane with polyoxyethylene and/or polyoxypropylene side chains having a molecular weight of from 10,000 to 50,000 and having the structure:

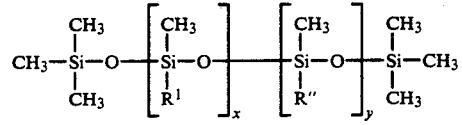

where the groups R' and R" are each chosen from —H, $C_{1-18}$ alkyl and

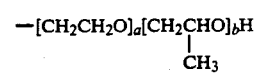

a has a value of from 9 to 115,
b has a value of from 0 to 50,
x has a value of from 133 to 673,
y has a value of from 25 to 0.25.

Preferably, the dimethyl polysiloxane polymer is one in which:
a has a value of from 10 to 114
b has a value of from 0 to 49
x has a value of from 388 to 402
y has a value of from 15 to 0.75
one of groups R' and R" being lauryl, and the other having a molecular weight of from 1000 to 5000.

A particularly preferred dimethyl polysiloxane polymer is one in which:
a has the value 14
b has the value 13
x has the value 249
y has the value 1.25

The dimethyl polysiloxane polymer is conveniently provided as a dispersion in a volatile siloxane, the dispersion comprising, for example, from 1 to 20% by volume of the polymer and from 80 to 99% by volume of the volatile siloxane. Ideally, the dispersion consists of a 10% by volume of the polymer dispersed in the volatile siloxane.

Examples of the volatile siloxanes in which the polysiloxane polymer can be dispersed include polydimethyl siloxane (pentamer and/or hexamer).

A particularly preferred silicone surfactant is cyclomethicone and dimethicone copolyol, such as DC 3225C Formulation Aid available from DOW CORNING. Another is laurylmethicone copolyol, such as DC Q2-5200, also available from Dow Corning.

The amount of silicone surfactant, when present in the composition will normally be up to 25%, preferably from 0.5 to 15% by weight of the emulsion.

Other Cosmetic Adjuncts

Examples of conventional adjuncts which can optionally be employed include preservatives, such as parahydroxy benzoate esters; antioxidants, such butyl hydroxy toluene; humectants, such as glycerol, sorbitol, 2-pyrrolidone-5-carboxylate, dibutylphthalate, gelatin, polyethylene, glycol, preferably PEG 200–600; buffers, such as lactic acid together with a base such as triethanolamine or sodium hydroxide; surfactants, such as glycerol ethers and other ceramides of synthetic, animal or plant origin; phospholipids; waxes, such as beeswax, ozokerite wax, paraffin wax, plant extracts, such as Aloe vera, cornflower, witch hazel, elderflower, cucumber; thickeners; activity enhancers; colourants; perfumes; and sunscreen materials such as ultrafine titanium dioxide and organic sunscreens such as p-aminobenzoic acid and esters thereof, ethylhexyl p-methoxycinnamate, 2-ethoxyethyl p-methoxycinnamate and butyl methoxydibenzoylmethane, and mixtures thereof.

In a further preferred composition, the pseudoceramide, or a mixture thereof, is combined with conventional ceramides, cholesterol, cholesterol fatty acids, fatty acids, triglycerides, cerebroside, phospholipid and other ingredients well known to those skilled in the art to produce a liposomal dispersion.

In yet another preferred composition, the pseudoceramide, or a mixture thereof, is dissolved in squalene or squalane, optionally together with conventional ceramides, and formulated with volatile and non volatile silicones to produce an anhydrous or nearly anhydrous single phase system.

Cosmetic adjuncts can form the balance of the composition.

Use of the Composition

The composition according to the invention is intended primarily as a product for topical application to human skin, especially as an agent for reducing the permeability to water of the skin, particularly when the skin is dry or damaged, in order to reduce moisture loss and generally to enhance the quality and flexibility of skin. The composition can also be applied to hair and nails.

The modified pseudoceramides according to the invention have surfactant properties and can therefore also be used, in the form of a composition as herein defined, for cleansing the surface of the human body. In particular the composition can be used to cleanse the skin to remove make up or can be employed in a shampoo for cleansing the hair.

In use, a small quantity of the composition, for example from 1 to 5 ml, is applied to exposed areas of the skin, from a suitable container or applicator and, if necessary, it is then spread over and/or rubbed into the skin using the hand or fingers or a suitable device.

In Vitro Measurement of Water Vapour Transmission Rate

The reduction in water permeability of the skin following topical application of the composition according to the invention can be determined by in vitro measurement of the water vapour transmission rate (WVTR) using a water transmission cell adapted from that described by Blank I.H., J. Invest. Dermatol., [1952], 18, 433–440.

Pretreatment of Porcine Stratum Corneum

Isolated porcine stratum corneum was floated on propan-2-ol contained in a glass petri dish. The dish was gently agitated for 4 hours at 40° C. and the sample of extracted stratum corneum was then removed, floated in saline solution onto spectra mesh and air dried overnight.

Measurement of Initial WVTR Prior to Treatment

850 $\mu$l distilled water was placed in the centre well of the cell and a sample of pretreated stratum corneum (see above) was carefully laid onto a stainless steel grid over the well ensuring that the stratum corneum completely covered the O-ring, such that a watertight seal was achieved. Care was taken to avoid wrinkles, tears and holes in the stratum corneum sample. The transmission cell was then screwed into position and allowed to equilibrate at room temperature before an initial measurement was made. The cell was weighed after 5 minutes, then placed in an incubator at 37° C., 0% RH. Two further weight measurements were taken at suitable intervals over a period of 24 hours at the end of which time a test or control solution was applied and two more measurements were taken during a further 21 hours. Five cells were used for each test or control treatment.

Study of the Effect of Topical Application of Test Material

For each test, a solution of test material in chloroform/methanol (2:1 v/v) was prepared at 24 mg/ml concentration. 10 $\mu$l of this solution was applied to the previously selected propan-2-ol extracted skin samples as described above. The chloroform/methanol quickly evaporated. The five cells containing the skin samples were weighed after 5 minutes prior to placing in the incubator at 37° C., 0% RH. As mentioned above, two weight measurements were then taken at intervals over a period of 21 hours.

A control measurement was made using other selected skin samples. This was carried out in the same way using an equal quantity of chloroform/methanol (2:1) containing no test material.

Calculation of the WVTR

The WVTR was calculated for each sample (pre and post topical application) as follows.

$$\text{WVTR (mg/cm}^2\text{/hr)} = \frac{\text{weight loss}}{\text{Area of exposed tissue} \times \text{time}}$$

The mean WVTR for each group of cells was then calculated from these values. The standard deviation was calculated from the observed changes (relative increase or decrease) in WVTR measured before and after the topical application.

Statistics

The level of significance was calculated using Duncan's Multiple Range test between WVTR measurements.

Results

The above procedure was used to assess the ability of solutions of a pseudoceramide, namely N-(2-hydroxy-3-hexadecyloxypropyl)-N-(2-hydroxyethyl)-2-hydroxyhexadecamide (Pseudoceramide structure 4) to reduce WVTR.

These were compared with controls using chloroform/ methanol alone, and positive controls using natural stratum corneum lipid in chloroform/methanol. Concentration of the natural lipid was again 24 mg/ml. The comparison was done twice. The first comparison also used a solution of N-(2-hydroxy-3-hexadecyloxypropyl)-N-(2-hydroxyethyl) hexadecamide which is representative of compounds of the known structure (1). Concentration was again 24 mg/ml.

| WVTR Values in mgs/cm$^2$/hr. with Standard Deviation | | |
|---|---|---|
| | before topical application | after topical application |
| First Experiment | | |
| a) Control (CHCl$_3$: MeOH only) | 12.37 ± 1.41 | 11.56 ± 1.84 |
| b) Skin lipid positive control (24 mgs/ml in CHCl$_3$: MeOH) | 13.10 ± 2.27 | 8.69 ± 1.50 |
| c) N-substituted hexadecamide of structure (1) (24 mgs/ml in CHCl$_3$: MeOH) | 10.17 ± 2.57 | 7.02 ± 1.44 |
| d) Pseudoceramide 4 (24 mgs/ml CHCl$_3$: MeOH) | 10.23 ± 3.47 | 5.58 ± 1.83 |
| Repeat Experiment | | |
| a) Control (CHCl$_3$: MeOH only) | 7.75 ± 4.13 | 7.58 ± 4.60 |
| b) Skin lipid positive control (24 mgs/ml in CHCl$_3$: MeOH) | 8.28 ± 5.17 | 4.07 ± 1.64 |
| c) Pseudoceramide 4 (24 mgs/ml in CHCl$_3$: MeOH) | 9.49 ± 2.68 | 5.38 ± 1.18 |

These experiments show that pseudoceramide of structure 4 reduced the WVTR of the skin sample to which it was applied to a greater extent than the known compound (45% compared with 31%).

PRODUCT FORM AND PACKAGING

The topical skin and/or hair treatment composition of the invention can be formulated as a lotion having a viscosity of from 4,000 to 10,000 mPas, a fluid cream having a viscosity of from 10,000 to 20,000 mPas or a cream having a viscosity of from 20,000 to 100,000 mPas, or above. The composition can be packaged in a suitable container to suit its viscosity and intended use by the consumer. For example, a lotion or fluid cream can be packaged in a bottle or a roll-ball applicator or a propellant-driven aerosol device or a container fitted with a pump suitable for finger operation. When the composition is a cream, it can simply be stored in a non-deformable bottle or squeeze container, such as a tube or a lidded jar.

The invention accordingly also provides a closed container containing a cosmetically acceptable composition as herein defined.

EXAMPLES

The invention is illustrated by the following examples.

EXAMPLE 1

This example illustrates a high internal phase water-in-oil emulsion in accordance with the invention.

A high internal phase water-in-oil emulsion having the following formulation was prepared:

| | % w/w |
|---|---|
| Fully hydrogenated coconut oil | 3.9 |
| Pseudoceramide having the structure (5) | 0.1 |
| Brij 92* | 5 |
| Bentone 38 | 0.5 |
| Preservative | 0.3 |
| MgSO$_4$7H$_2$O | 0.3 |
| Butylated hydroxy toluene | 0.01 |
| Perfume | qs |
| Water | to 100 |

*Brij 92 is polyoxyethylene (2) oleyl ether

EXAMPLE 2

This example also illustrates a high internal phase water-in-oil emulsion in accordance with the invention in which the formulation of Example 1 was prepared but with the following changes:
i. liquid paraffin replaced the fully hydrogenated coconut oil, and
ii. the pseudoceramide had the structure (6).

EXAMPLE 3

This example also illustrates a high internal phase water-in-oil emulsion in accordance with the invention in which the formulation of Example 1 was prepared but with the following changes:
The pseudoceramide had the structure (7).

EXAMPLE 4

This example illustrates an oil-in-water cream containing an ester of the invention.

An oil-in-water cream emulsion having the following formulation was prepared:

| | % w/w |
|---|---|
| Mineral oil | 4 |
| Pseudoceramide having the structure (8) | 0.1 |
| Brij 56* | 4 |
| Alfol 16RD* | 4 |
| Triethanolamine | 0.75 |
| Butane-1,3-diol | 3 |
| Xanthan gum | 0.3 |
| Preservative | 0.4 |
| Perfume | qs |
| Butylated hydroxy toluene | 0.01 |
| Water | to 100 |

*Brij 56 is cetyl alcohol POE (10)
Alfol 16RD is cetyl alcohol

EXAMPLE 5

This example also illustrates an oil-in-water emulsion containing a compound of the invention, in which the formulation of example 4 was prepared but with the following change:

the pseudoceramide was that having structure (9), as herein defined.

EXAMPLE 6

This example also illustrates an oil-in-water emulsion in accordance with the invention, in which the formulation of example 4 was prepared but with the following changes:
pseudoceramide was that having the structure (10) as herein defined.

EXAMPLE 7

This example illustrates an alcoholic lotion containing an amide of the invention.
The lotion had the following formulation:

|  | % w/w |
| --- | --- |
| Pseudoceramide having the structure (11) | 0.2 |
| Ethanol | 40 |
| Perfume | qs |
| Butylated hydroxy toluene | 0.01 |
| Water | to 100 |

EXAMPLE 8

This example illustrates an alcoholic lotion containing an amide of the invention.
The lotion had the following formulations:

|  | % w/w |
| --- | --- |
| Pseudoceramide having the structure (12) | 0.2 |
| Dimethylsulphoxide | 10 |
| Ethanol | 40 |
| Antioxidant | 0.1 |
| Perfume | qs |
| Water | to 100 |

EXAMPLES 9 and 10

The following compositions according to the invention represent lotions which can be used in the treatment of dry skin:

|  | % w/w | |
| --- | --- | --- |
|  | 9 | 10 |
| Pseudoceramide having the structure (13) | 1.5 | — |
| Pseudoceramide having the structure (14) | — | 0.5 |
| Perfume | 0.1 | 0.1 |
| Hydroxyethyl cellulose | 0.4 | 0.4 |
| Absolute ethanol | 25 | 25 |
| p-methyl benzoate | 0.2 | 0.2 |
| Sterilised demineralised water | to 100 | to 100 |

EXAMPLES 11 and 12

The following compositions according to the invention represent lotions which can be used in the treatment of dry skin:

|  | % w/w | |
| --- | --- | --- |
|  | 11 | 12 |
| The pseudoceramide having the structure (15) | 0.08 | — |
| The pseudoceramide having the structure (16) | — | 0.15 |
| Ethanol | 10 | 10 |
| Perfume | 0.5 | 0.5 |
| Distilled water | to 100 | to 100 |

EXAMPLE 13

This example illustrates a high internal phase water-in-oil emulsion in accordance with the invention.
A high internal phase water-in-oil emulsion having the following formulation was prepared:

|  | % w/w |
| --- | --- |
| Fully hydrogenated coconut oil | 3.9 |
| Pseudoceramide having the structure (4) | 0.1 |
| Brij 92* | 5 |
| Bentone 38 | 0.5 |
| Preservative | 0.3 |
| $MgSO_4 7H_2O$ | 0.3 |
| Butylated hydroxy toluene | 0.01 |
| Perfume | qs |
| Water | to 100 |

*Brij 92 is polyoxyethylene (2) oleyl ether

EXAMPLE 14

This example also illustrates a high internal phase water-in-oil emulsion in accordance with the invention in which the formulation of Example 1 was prepared but with the following changes:
i. liquid paraffin replaced the fully hydrogenated coconut oil, and
ii. the pseudoceramide had the structure (5).

EXAMPLE 15

This example also illustrates a high internal phase water-in-oil emulsion in accordance with the invention in which the formulation of Example 1 was prepared but with the following changes:
The pseudoceramide had the structure (6).

EXAMPLE 16

This example illustrates an oil-in-water cream containing a compound of the invention.
An oil-in-water cream emulsion having the following formulation was prepared:

|  | % w/w |
| --- | --- |
| Mineral oil | 4 |
| Pseudoceramide having the structure (7) | 0.1 |
| Brij 56* | 4 |
| Alfol 16RD* | 4 |
| Triethanolamine | 0.75 |
| Butane-1,3-diol | 3 |
| Xanthan gum | 0.3 |
| Preservative | 0.4 |
| Perfume | qs |
| Butylated hydroxy toluene | 0.01 |
| Water | to 100 |

*Brij 56 is cetyl alcohol POE (10)
Alfol 16RD is cetyl alcohol

EXAMPLE 17

This example also illustrates an oil-in-water emulsion containing an ester of the invention, in which the formulation of example 4 was prepared but with the following change:
the pseudoceramide was that having structure (8), as herein defined.

EXAMPLE 18

This example also illustrates an oil-in-water emulsion in accordance with the invention, in which the formulation of example 4 was prepared but with the following changes:
  pseudoceramide was that having the structure (9) as herein defined.

EXAMPLE 19

This example illustrates an alcoholic lotion containing an amide of the invention.
The lotion had the following formulation:

|  | % w/w |
|---|---|
| Pseudoceramide having the structure (10) | 0.2 |
| Ethanol | 40 |
| Perfume | qs |
| Butylated hydroxy toluene | 0.01 |
| Water | to 100 |

EXAMPLE 20

This example illustrates an alcoholic lotion containing an amide of the invention which is suitable for application to nails.
The lotion had the following formulations:

|  | % w/w |
|---|---|
| Pseudoceramide having the structure (11) | 0.2 |
| Dimethylsulphoxide | 10 |
| Ethanol | 40 |
| Antioxidant | 0.1 |
| Perfume | qs |
| Water | to 100 |

EXAMPLES 21 and 22

The following compositions according to the invention represent lotions which can be used in the treatment of dry, unmanageable hair.

|  | % w/w | |
|---|---|---|
|  | 21 | 22 |
| Pseudoceramide having the structure (12) | 1.5 | — |
| Pseudoceramide having the structure (13) | — | 0.5 |
| Perfume | 0.1 | 0.1 |
| Hydroxyethyl cellulose | 0.4 | 0.4 |
| Absolute ethanol | 25 | 25 |
| p-methyl benzoate | 0.2 | 0.2 |
| Sterilised demineralised water | to 100 | to 100 |

EXAMPLES 23 and 24

The following compositions according to the invention represent lotions which can be used in the treatment of dry skin, hair or nails:

|  | % w/w | |
|---|---|---|
|  | 23 | 24 |
| The pseudoceramide having the structure (14) | 0.08 | — |
| The pseudoceramide having the structure (15) | — | 0.15 |
| Ethanol | 10 | 10 |
| Perfume | 0.5 | 0.5 |
| Distilled water | to 100 | to 100 |

What is claimed is:

1. A synthetic pseudoceramide having the structure (2):

$$R-(CHOR^2)_a-(CH_2)_b-\overset{O}{\underset{\|}{C}}-\underset{R^3}{\overset{|}{N}}-CH_2-\overset{R^1-O-CH_2}{\underset{CHOR^2}{|}} \quad (2)$$

where
R represents a linear or branched, saturated or unsaturated, hydroxylated or non-hydroxylated, phosphorylated or non-phosphorylated, sulphated or non-sulphated aliphatic hydrocarbon group having from 1 to 49 carbon atoms;
$R^1$ represents a linear or branched, saturated or unsaturated, hydroxylated or non-hydroxylated, phosphorylated or non-phosphorylated, sulphated or non-sulphated aliphatic hydrocarbon group having from 1 to 28 carbon atoms;
$R^2$ represents H, a sugar residue, a sulphate residue or a phosphate residue $P_i$;
$P_i$ represents the group:

$$-\overset{O^\ominus}{\underset{O^\ominus}{\overset{|}{\underset{|}{P}}}}=O$$

$R^3$ represents H, or the sub group (3):

$$-(CH_2)_c-\left[\overset{X^1}{\underset{X^2}{\overset{|}{\underset{|}{C}}}}\right]_d-\overset{X^3}{\underset{|}{C}}H\,OR^2$$

$X^1$, $X^2$ and $X^3$ each individually represent H, $C_{1-5}$ alkyl or $C_{1-5}$ hydroxyalkyl;
a is 1
b is 0 or 1
c is 0 or an integer of from 1 to 4
d is 0 or 1.

2. A process for synthesising the pseudoceramide according to claim 1 which comprises the steps of:
  i. ring opening the epoxide ring of a glycidyl ether having the formula $$R^1OCH_2CH\overset{O}{\overset{\diagup\ \diagdown}{\underset{}{\phantom{X}}}}CH_2$$

with an amine of formula $RNH_2$ to yield the corresponding secondary amine; and
  ii. acylating the secondary amine with an ester or acid chloride of a hydroxylated fatty acid or a non-hydroxylated fatty acid with less than 10 carbon atoms to yield the pseudoceramide.

3. A composition suitable for topical application to skin, hair or nails, which comprises:
  i. an amount of from 0.0001 to 20% by weight of the pseudoceramide according to claim 1; and
  ii. a cosmetically acceptable vehicle for the pseudoceramide.

4. A method of treating skin, hair or nails which comprises applying topically thereto a composition containing a pseudoceramide according to claim 1.

5. A method of treating skin, hair or nails which comprises applying topically thereto a composition according to claim 3.

6. A method according to claim 4 wherein the application is to skin.

* * * * *